(12) United States Patent
Burtscher et al.

(10) Patent No.: US 7,682,426 B2
(45) Date of Patent: Mar. 23, 2010

(54) METHOD AND DEVICE FOR THE DETECTION, CHARACTERIZATION AND/OR ELIMINATION OF SUSPENDED PARTICLES

(75) Inventors: Heinz Burtscher, Rudolfstetten (CH); Markus Kasper, Widen (CH); Ulrich Matter, Baden (CH)

(73) Assignee: Matter Engineering AG, Wohlen (CH)

( * ) Notice: Subject to any disclaimer, the term of this patent is extended or adjusted under 35 U.S.C. 154(b) by 1273 days.

(21) Appl. No.: 10/819,832

(22) Filed: Apr. 7, 2004

(65) Prior Publication Data
US 2004/0202578 A1    Oct. 14, 2004

(30) Foreign Application Priority Data
Apr. 11, 2003    (EP)    .................................. 03405248

(51) Int. Cl.
*B01D 53/00*    (2006.01)
(52) U.S. Cl. .................. 95/288; 261/78.2; 261/128; 73/863.11; 73/863.12; 73/863.21
(58) Field of Classification Search .............. 73/863.11, 73/863.12, 863.21, 78.2; 261/78.2, 128, 261/141; 422/83; 356/337; 250/573; 95/288
See application file for complete search history.

(56) References Cited
U.S. PATENT DOCUMENTS
3,644,743 A * 2/1972 Binek et al. .................. 250/575

5,109,708 A * 5/1992 Lawless ..................... 73/863.11
5,156,776 A * 10/1992 Loedding et al. ............... 261/27
6,439,027 B1    8/2002 Hiss, III FOREIGN PATENT DOCUMENTS
EP    1 251 344 A2    10/2002
JP    01195341 A * 8/1989 ................. 73/61.71

OTHER PUBLICATIONS
WO 01/84116 A1, Method and Device for the Extractive Triboelectric Measurement of Dust and Aerosols in Streaming Gases, Publication Date: Nov. 8, 2001.

* cited by examiner

*Primary Examiner*—Robert A Hopkins
(74) *Attorney, Agent, or Firm*—Rankin, Hill & Clark LLP

(57) ABSTRACT

Volatile suspended particles are eliminated from an aerosol by heating the aerosol to a temperature at which the volatile suspended particles evaporate and diluting the aerosol with a dilution gas. The sequence heating and diluting may be performed in any order. According to another aspect of the invention, dilution of the raw gas takes place such that raw gas is led to a measurement gas channel through which measurement gas flows, wherein the quantity of raw gas transferred per unit of time is dependent on the volume flow in the raw gas channel. According to a further aspect of the invention, in a condensation nucleus counter the number and intensity of scattered light pulses evaluated in order to be able to draw conclusions on the reliability of the measurement.

3 Claims, 4 Drawing Sheets

METHOD AND DEVICE FOR THE DETECTION, CHARACTERIZATION AND/OR ELIMINATION OF SUSPENDED PARTICLES

BACKGROUND OF THE INVENTION

The invention lies in the field of detection, characterization and/or elimination of suspended particles in a carrier gas. In particular, it relates to a method and to a device for characterizing, separating and/or eliminating suspended particles in a carrier gas.

Waste gas from emission sources in the household, private transport, goods transport and industry contain suspended particles. A substance mixture of suspended particles and a carrier gas is often called an aerosol. Submicroscopic suspended particles are of particular concern to the public since they may have access to the lungs and may affect the health.

For characterizing emission sources and measurements of suspended particles in waste gases, in a first step an unadulterated sample must be obtained whose suspended particle concentration permits conclusions to be drawn on the quantity of the harmful suspended particles emitted by the emission source. Furthermore, a measuring method should be available which permits an as convincing as possible characterization of the suspended particles whilst taking their noxiousness into account.

Traditional gravimetric methods are used for the particle measurement. The mass of particles for example filtered by or in a filter is measured and serves as an indicator for the noxiousness of a waste gas. The disadvantage is the fact that the small and middle-sized particles are attributed a low weight by this method, and it is those small and middle-sized particles which are particularly harmful due to their access to the lung in contrast to the larger particles.

With the measurement of particle emissions of motors and vehicles, the number instead of the total weight of the emitted particles is therefore significant as a characteristic quantity.

It would be desirable to have at one's disposal a measurement method and a corresponding device which provide measurement results which are more balanced with regard to noxiousness than gravimetric measurements and which for example determine the particle number instead of their total mass. This is also demanded with respect to the creation of new waste gas standards (for example with the projects sketch Particulate Measurement Program (PMP) of UNECE/GPPE). A measurement device should furthermore be as inexpensive and as compact as possible so that it may be applied in measurement test beds of local traffic offices and automobile garages etc.

The invention proceeds along the path of a measurement method and device which fulfils these conditions.

Measurement methods for determining the particle number are known per se. However, the follow problems arise:

1. Dilution: One may never measure the complete flow of waste gas, but a sample should be able to be taken whose suspended particle concentration permits conclusions to be drawn with regard to the total emitted suspended particle quantity. According to the state of the art, a so-called full flow diluter is often arranged upstream of the measurement system. All waste gas is supplied to the measurement line. Additionally, so much dilution gas is admixed that the volume flow in the measurement line is constant independently of the waste gas quantity. In this manner it is achieved that the concentration of the suspended particles in the measurement line is proportional to the emitted total particle quantity. For measurement, any magnitude of part quantity needs to be diverged from the gas in the measurement line and the particle concentration contained therein determined. The measurement systems based on full flow dilution are however very complicated, large and expensive since a very large gas volume needs to be dealt with (the volume flow in the measurement line indeed must be larger than the maximal waste gas flow, e.g. at full load of the motor).

2. Volatile suspended particles: With the suspended particles it is the case of volatile and solid substances. Such a situation is present with diesel exhaust. With diesel exhaust, the solid dust particles consist mainly of carbon, the volatile particles of condensed hydrocarbons and/or sulphuric acid and water. In many cases, it is desirable to separate the volatile from the solid suspended particles or to eliminate the volatile suspended particles. For example, when considering respiratory diseases, it is chiefly the solid suspended particles that contribute to the noxiousness of the waste gas. Furthermore, with regard to the noxiousness of volatile suspended particles, the extent of their noxiousness is the subject-matter of current trials and examinations,—other measurement criteria are significant. Their number to the first degree is not relevant but their total mass.

For eliminating the volatile suspended particles form the measurement gas there are a few starting points known from the state of the art:

Thermodesorber: The thermodesorber (often also called as thermodenuder) is an apparatus known for several years and commercialized by various suppliers (TSI/Topas; Dekati), for removing volatile particles from an aerosol. The thermodesorber consists of a heated tube in which the aerosol is brought to a defined temperature and thus volatile aerosol components may be evaporated. A so-called activated carbon trap is connected to this, in which the aerosol vapor mixture is led through a tube with wire grating walls on the outside of which an activated carbon (granulated material) is located. Vapor molecules of the volatile aerosol components on account of their strong diffusion movement advance up to the activated carbon granules where they are absorbed and thus removed from the aerosol. The solid, non-evaporated aerosol particles follow the gas flow through the tube with the grating walls. Behind the activated carbon trap, the aerosol on account of the absorption by the activated carbon, contains only such a small amount of vapors that the vapors condense to no or to an insignificant extent. The removal of volatile aerosol components under unfavorable conditions depends on the saturation degree of the activated carbon.

Ejector-diluters (Dekati): The Finnish company Dekai supplies so-called ejector diluters with which the raw aerosol is led through a nozzle and entrained by a rapid dilution air flow. The disadvantages of the ejector method are the narrow setting range of the dilution conditions and its dependence on the pressure conditions.

Measurement difficulties with small particles: Common measurement methods have their limits when counting very small suspended particles which may be significant which regard to their number.

One method for counting suspended particles which is common per se is based on the light scatter of these particles on passage through a light beam. For this, the particles are blown through the continuous light beam by way of a nozzle. By way of suitably dimensioning the nozzle diameter, particle concentration and light beam diameter, one may ensure that, in each case, only a single particle is located in the light beam. With its passage through the light beam, a particle scatters the light in spatial directions outside the beam direction. Photodiodes, which are arranged in these spatial directions, thus detect the rise in the light intensity during the passage of the particle. The number of the thus measured scatter light pulses is thus equal to the number of particles which are jetted into the counting optics.

The intensity of the scattered light is heavily dependent on the size of the particles. Below a particle size of 200-300 nm a detection of the scatter light signal is very complex and practically no longer possible. For this reason, the method of particle counting via light scattering is often applied in combination with so-called condensation nucleus counters (CNC). Since the particles in the submicron region escape the counting with optical methods on account of the low intensity of the light scattered by them, they are "enlarged" in the condensation nucleus counter until they provide a scatter light signal which is sufficient for a counting. For this reason, the aerosol containing submicron particles is firstly led over the saturated vapor of the fluid. Subsequently, by way of strong cooling in a condenser, a supersaturation of the vapor is produced, which as a result of this condenses on the available surfaces, amongst others on the particles. The diameter to which the droplets condense on the particles at the end of the condensation procedure, is largely dependent on the original size of the aerosol particles.

Butanol is often used as an evaporated-on fluid. The particle-containing gas firstly flows through a heated path (35° C.) over a butanol bath. At the same time, the gas is saturated with butanolvapor. Subsequently, a cooled part (condenser, 10° C.) follows, where the vapor is supersaturated due to the reduced temperature and condenses on the particles. The particles thus grow to droplets of typically about 10 µm diameter.

The droplet formation, however, only functions above a certain minimum diameter of the introduced aerosol particles. The supersaturation may only be so large that no homogenous nucleation, that is to say droplet formation without condensation nucleus, occurs. On the other hand, the supersaturation should be as large as possible so that also very small particles may grow (vapor pressure increase with small particles). With a given supersaturation the minimal diameter D is determined by the Kelvin-Gibbs equation:

$$Dk=4\sigma M/(RT \rho \ln(S))$$

(Dk: Kelvin-diameter
σ: surface tension
M: molar mass of the vapour molecules
σ: density of the fluid
R: gas constant
S: supersaturation).

The equation applies to droplets of the material of thevapor, thus only if at least one monolayer of vapor is already adsorbed on the particle. The condition that this monolayer arises is dependent on the particle surface.

For the condensation nucleus counter (CNC) this means:
1. The conditions for forming the first layer must be fulfilled (dependent on the particle material, surface structure).
2. The critical supersaturation must be achieved or D>Dk so that the particle may continue to grow.

Apart from these phenomena, diffusion losses in the CNC may yet further disturb the measurement of very small particles.

Typical lower limits for the particle size lie at 20 nm or even smaller. Today, there are already models which still have 50% efficiency at 3 nm. The end size of the droplet arising in the CNC is largely dependent on the particles size.

With the measurement of particles from motor or vehicle emissions, it may occur that, e.g. due to the formation of condensation products on taking the sample, a not insignificant share of the particles are located in the vicinity of this diameter-related sensitivity threshold of the condensation nucleus counter. The measurement result then depends greatly on the momentary and usually non-stable size distribution of the particles and is, thus, no longer reliable.

SUMMARY OF THE INVENTION

The invention therefore poses the following objects:

A first object of the invention to provide a device for separating volatile suspended particles so that only the solid dust particles remain for an advanced characterization or processing of the aerosol. The device should avoid the disadvantages of existing devices and in particular be simple in manufacture and handling, should function reliably and should permit as large as possible elimination of the volatile suspended particles.

A second object of the invention is to provide a method and a device that minimize the disturbing influencing factors with temporally critical particulate measurement of changing volume flows, and that distance themselves from the disadvantageous full flow dilution.

A further object of the invention is to provide a method and a device that permits the conditions to be determined under which the measurement is no longer reliable and, as the case may be, needs to be supplemented by further methods.

The method provided with regard to a first aspect of the invention for separating volatile suspended particles and the corresponding device are based on a heating path and a dilution unit. The device for example comprises a) a heating path and a dilution unit arranged downstream, or
b) the dilution unit and a heating path arranged downstream.

The temperature of the aerosol is increased in the heating path in a manner such that its volatile constituents change over into the gas. Thus, at the end of the heating path, a changed substance mixture is, thus, present in which only the non-evaporated substances are still present as particles, the volatile substances, however, are present asvapors.

In the dilution system, by way of admixing particle-free carrier gas to the aerosol, the concentration of the particles and droplets is reduced whilst the material composition of the particles or share of volatile droplets to solid particles do not change. For the carrier gas free of particles used for the dilution, it may be assumed that the share of substances contained therein, which are present in the aerosol as droplets orvapors, is negligibly low. The dilution process therefore leads to a reduction of the vapor pressure of such substances. The complete dilution unit and the particle-free carrier gas used for dilution may be heated.

With an arrangement according to a) (dilution unit arranged downstream) the volatile substances are firstly evaporated in the heating path. By way of the dilution arranged downstream, not only is the concentration of the solid particles reduced, but also the vapor pressure of the volatile substances present in the vapor phase at this location. By way of setting a sufficient dilution, this vapor pressure may be reduced to such an extent that the volatile substances no longer condense, even with a subsequent cooling to the original temperature of the aerosol. The substance mixture exiting this arrangement, thus, only contains solid particles.

With an arrangement according to b) (dilution unit arranged upstream) the concentration of solid particles, as well as volatile droplets, is firstly reduced in the dilution unit.

In the heating path arranged downstream, the volatile substances are then conveyed into the vapor phase. By way of setting a sufficient dilution the concentration of the volatile droplets may be reduced such that after evaporation in the heating path, the vapor pressure of these substances is so low that they no longer condense, even with a subsequent cooling to the original temperature of the aerosol. The substance mixture exiting from this arrangement thus only contains solid particles.

According to a second aspect of the invention, it is the case of a method and a device that permit the dilution of the aerosol to be characterized and/or the preparation of a measurement gas, whose concentration of suspended particles is characteristic of the emitted total suspended particle quantity.

If one wishes to distance oneself from the complicated principle of full flow dilution, one must extrapolate from the sample volume taken for measurement to the total waste gas volume emitted by the installation. This demands a measurement of the volume flows in the measurement line, as well as in the main waste gas line, as well as their consideration on determining and evaluating data.

If the waste gas flow is a constant volume flow, then the data evaluation may be restricted to the multiplication of the measurement data by a proportionality factor. In certain cases, however, the waste gas volume flow is subjected to great temporal fluctuations, such as with the measurement of vehicle emissions during the travel cycle on the roller test bed. Additional time-critical influencing variables must then be taken into account for the correct evaluation of the data, like:

- the time shift between the volume flow measurement in the waste gas line and the occurrence of the corresponding particle cloud in the measurement instrument,
- the smearing caused by diffusion of (the flanks of) the particle cloud on the transport path to the measurement instrument,
- the response behavior of the measurement principle realized in the instrument to a rapidly changing particle concentration.

The second aspect of the invention fulfils these demands:

The reading of the volume flow measurement in the raw gas channel (the main line) is used in order to temporally vary the dilution condition in a dilution unit. By way of the dilution unit, raw gas is transferred in a metered manner from the raw gas channel into a measurement gas channel, wherein the transfer is controlled in a manner such that the quantity of raw gas that is transferred per unit of time is dependent on the volume flow in the raw gas channel and, thus, becomes larger as the volume flow in the raw gas channel becomes larger.

Accordingly, the dilution unit may be set such that a low dilution is effected given a high waste gas volume flow, but a high dilution is effected given a low waste gas volume flow. If the waste gas volume flow sinks to zero, then the dilution ratio becomes infinite, i.e. only particle-free dilution gas is led to the measurement instruments.

A measurement of the volume flows of waste gas (raw gas channel=main line) and measurement gas (measurement gas channel=auxiliary line) may be realized by way of various known measurement principles so that one may assume the availability of the measurement data obtainable therefrom.

According to a particularly preferred embodiment, the control is selected such that the particle flow exiting the dilution unit in its temporal course is exactly proportional to the particle flow in the waste gas line (possibly disregarding a slight time shift caused by the spatial distance of the volume flow measurement and dilution unit; this may e.g. be corrected electronically). It is thus ensured that the measurement instruments arranged after the dilution unit measure a temporal course of the particle concentration that corresponds exactly to the particle flow through the waste gas main line.

One embodiment of the dilution unit based on technology which has already been realized is a so-called rotating disc dilutor (or carrousel dilutor), with which a disc provided with cavities conveys small raw gas volumes into the particle-free dilution gas (such a rotating disc dilutor—type MD19-2E—may be obtained from the patent applicant, Matter Engineering AG; corresponding information is to be found in Ch. Hueglin, L. Scherrer and H. Burtscher, J. Aerosol Sci. 28, p.1049 (1997) or directly at the manufacturer). The slower the disc rotates, the less gas gets into the dilution flow, and the higher becomes the dilution ratio. The rotation frequency is determined from a setting value on the part of the user and, for example, the dilution gas flow, so that given an equal setting value and a changing measurement gas flow—for example the connectional arrangement of a further measurement instrument—the dilution conditions remain constant by way of adapting the rotation frequency.

The above-described control principle for the rotation frequency of the disc is then extended such that the volume flow measured in the waste gas line is also included in the computation of the rotation frequency. For example, with a static waste gas (corresponding to "motor off") a volume flow of zero is measured. The preset value for the rotation frequency is multiplied by the volume flow value (in this case zero) so that with a stationary waste gas, the disc also does not now rotate.

According to a third aspect of the invention, a method and a device are provided which likewise proceed with a comparatively compact characterization device for aerosols that is sensitive to the particle number. It is applied to condensation nucleus counters (CNC) with which the previously outlined problems with particles close to or below the critical size result.

If the aerosol particles introduced into the condensation nucleus counter fall short of a certain minimal size, then the condensation process with the given degree of supersaturation of the vapor may not set in or only slowly. The droplets condensed onto such small aerosol particles as a result have a significantly smaller diameter that those condensed on larger initial particles.

With the usual operating manner of condensation nucleus counters, it is ascertained whether a scatter light flash determined by the counter optics has a certain minimum intensity in order to take it into account as a signal of a particle on evaluation. Thus, the CNC measures the particle concentration, but itself does not provide any great information. This concentration, when required, must be obtained in combination with a movability analyzer or a diffusion battery.

According to a third aspect of the invention, which proceeds beyond a simple discrimination, the intensity of the scatter light pulse is detected so sensitively that the frequency distribution of the intensities may be determined.

Thus, this aspect of the invention makes use of the particularity that small droplets produce scatter signals of a considerably reduced intensity in the counter optics. The occurrence of light pulses of a lower intensity thus indicates the presence of smaller particles in the aerosol. "Small" here means "in the vicinity of the diameter-related detection threshold of the instrument".

If the relative frequency of "smaller" light pulses exceeds a certain measure, this indicates significant particle numbers in the region of the detection threshold so that one may no longer assume a reliable measurement of the total particle number.

This method is dependent on other parameters of the particle measurement and may therefore be used as an additional criterion for validating the result.

BRIEF DESCRIPTION OF THE DRAWINGS

Embodiment examples of the invention are hereinafter described in detail by way of drawings. In the drawings there are shown in.

DETAILED DESCRIPTION OF THE PREFERRED EMBODIMENT(S)

Figure 1A:
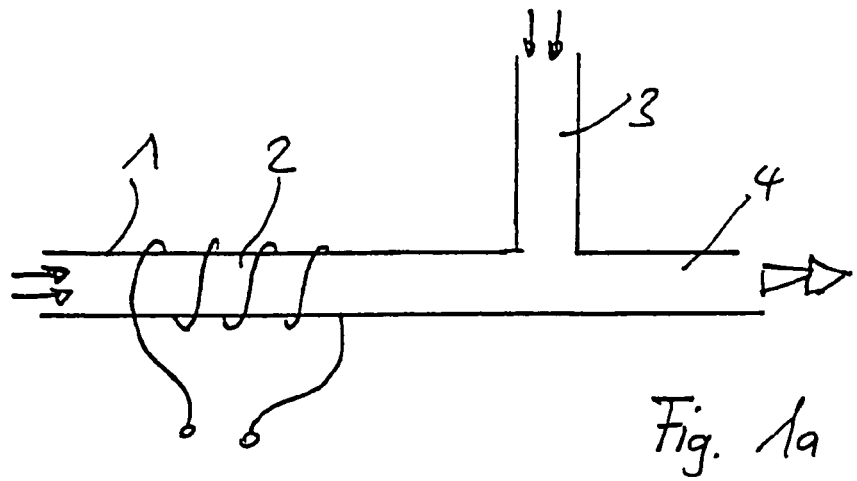
FIGS. 1a and 1b is in each case a schematic diagram of a first aspect of the invention.
Figure 1B:
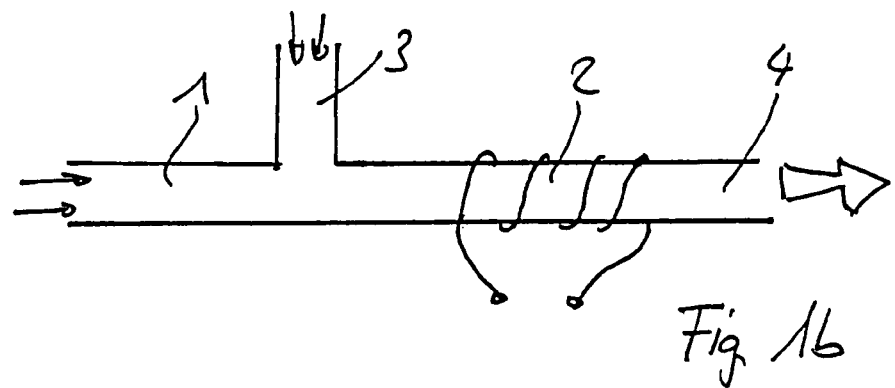

The embodiments of the invention according to FIGS. 1a and 1b are based on the principle of the full flow dilution. All gas flowing in from the raw gas channel is led to the measurement gas channel. A dilution unit in these cases thus merely consists of an admixture of dilution gas to the raw gas, wherein the dilution gas is preferably essentially free of suspended particles.

According to FIG. 1a, the gas containing suspended particles flowing into the raw gas channel 1 is heated so much on a heating path 2 that the volatile suspended particles evaporate. With combustion gases, the temperature required for this is usually at least approx. 180° C. or at least 200° C. The maximal temperature is dependent on the used raw materials and is, for example, approx. 400° C. since at higher temperatures catalytic effects occur on metal surfaces which may adulterate the measurement results. Preferred temperatures are, for example, approx. 190° C. to 350° C., particularly preferred is the range between 200° C. and 300° C. Heating means present on the heating path 2 may comprise a tube heating but other heating means are also conceivable, for example heating wires running in the gas channel.

Dilution gas is supplied via a dilution channel 3. The dilution channel opens out at a location in the raw gas channel at which the combustion gases located in this are still fully heated and, thus, are still located in the temperature range between 180° C. or 200° C. and 400° C. The dilution has the effect that the volatile evaporated aerosols no longer condense in the measurement channel 4.

The arrangement according to FIG. 1b differs from that according to FIG. 1a in that the dilution channel 3 is arranged in front of the heating path 2 in the flow direction.

The arrangements according to the FIGS. 1a and 1b which are shown only very schematically may be applied and modified in various manners:

For example the gas introduced into the raw gas channel must not be the total raw gas or that obtained as the combustion gas. Rather, it may be only a part of this gas. Methods and devices for diverging a well defined or arbitrary amount of gas from a first channel into a second channel are known in the art.

The gas quantity introduced into the dilution channel may be controlled for example such that the gas quantity flowing into the measurement gas channel 4 is always constant.

Deviating from the principle of the full flow dilution, also only a part of the raw gas together with dilution gas may be supplied to a measurement gas channel. For this, there follows yet one example further below, here in combination with the second aspect of the invention.

Figure 2:
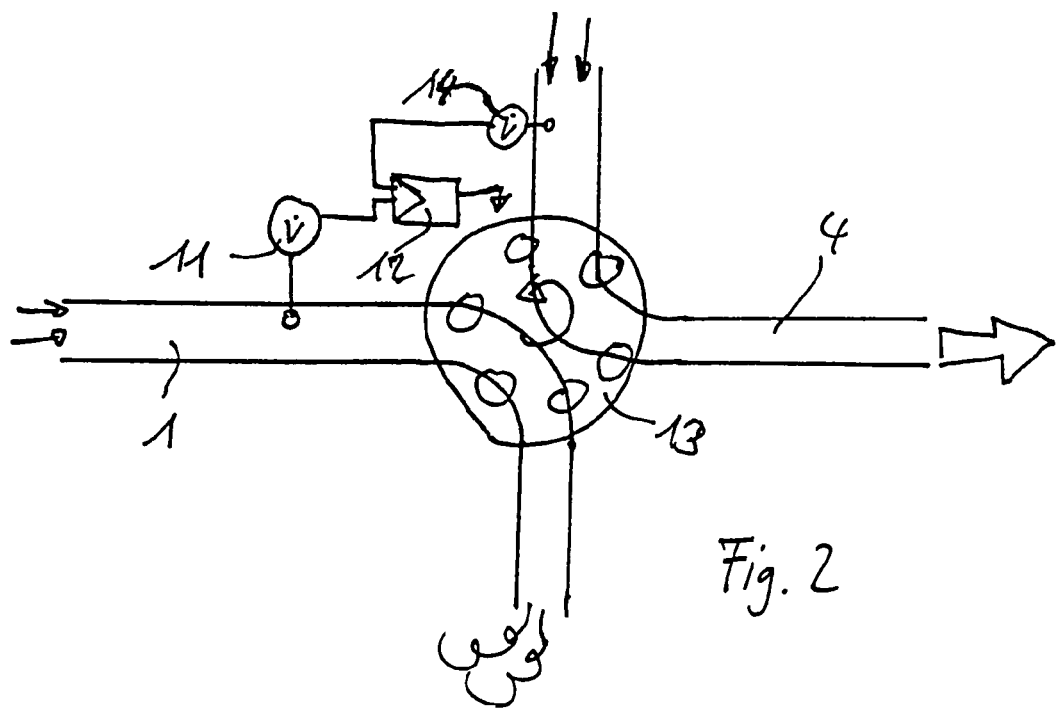
FIG. 2 is a schematic diagram of an embodiment of the second aspect of the invention.

One embodiment of the second aspect of the invention is shown in FIG. 2. Volume flow measurement means, for example a first measuring probe 11, evaluate the volume flow present in the raw gas channel 1. The measurement results are led to a controller 12. This controls a dilution unit, for example a carousel diluter 13 known per se. The dilution unit is arranged and designed such that only a part of the raw gas (for example waste gas) is led to the measurement gas channel 4. The control is effected such that the quantity of the raw gas led to the measurement gas channel 4 per unit of time becomes larger, the larger is the volume flow in the raw gas channel. According to a preferred embodiment, the raw gas quantity supplied to the measurement gas channel is proportional to the volume flow. The volume flow of the dilution gas flowing into the measurement gas channel 4 may be kept constant by way of suitable means (precise pumps, throttles). Alternatively, or to supplement this, volume flow measurement means, for example a second measuring probe 14 may be present in the measurement gas channel, wherein then the raw gas quantity supplied to the measurement gas channel is controlled such that it is also proportional to the volume flow of the dilution gas.

The measurement of the volume flows may also be effected in a manner known per se, for example with a hot-wire flowmeter, by way of the measurement of the pressure reduction by way of a Venturi tube, with a turbine flow measurement device, etc. One may, however, also envisage processing the data of the volume flow of the raw gas, which is known per se. Very precise data on the volume flow may, for example, be determined from the data present from the motor electronics of modern combustion motors, for example from the rotational speed and the charging pressure of the turbocharger. In this latter case, the means for determining the volume flow in the raw gas channel consist merely of electronic communication means that are connected to the electronics of the motor and extract volume flow data from the electronics.

Figure 3:
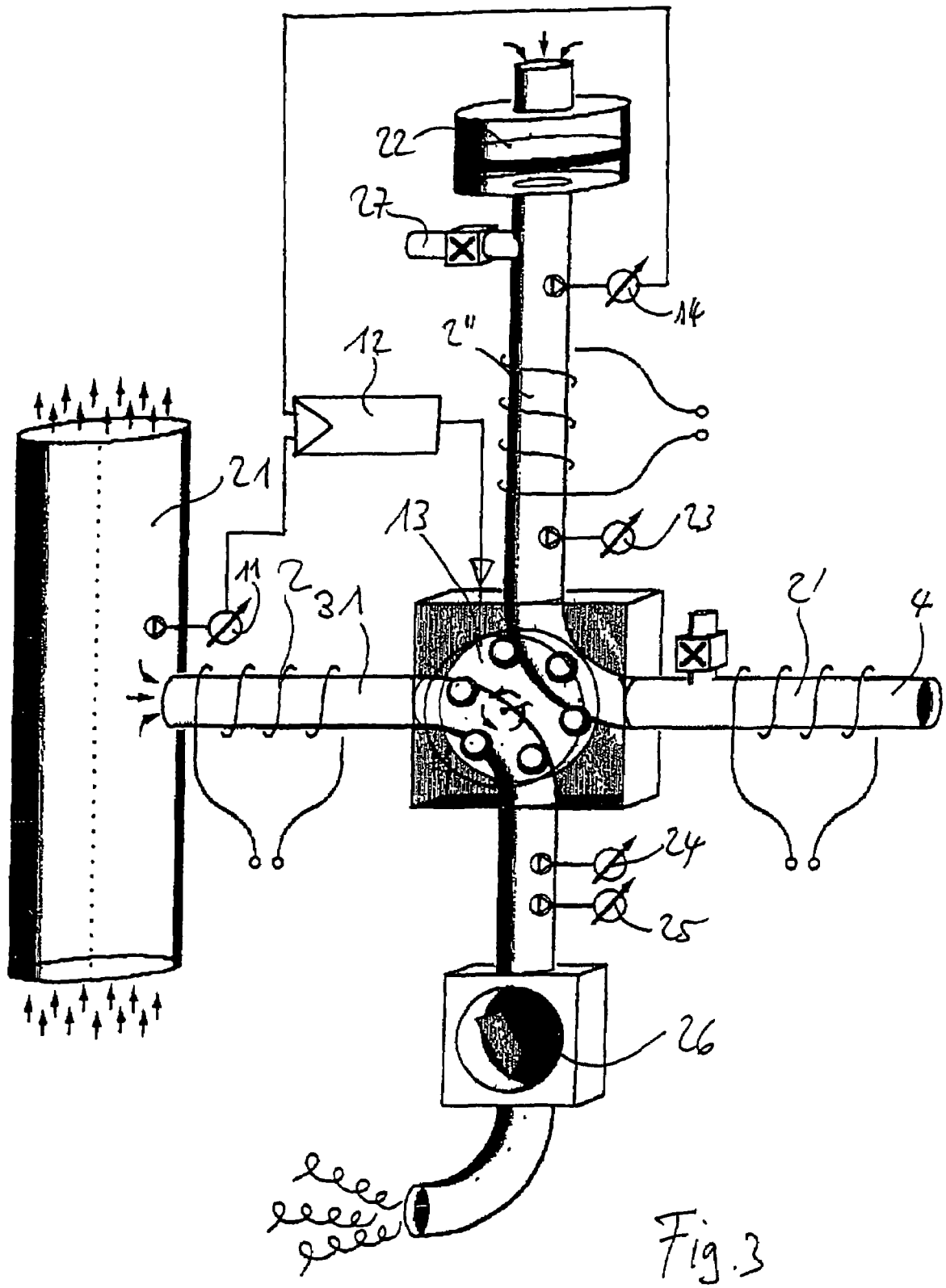
FIG. 3 is a schematic diagram of an arrangement for preparing measurement gas, which is free of volatile suspended particles and whose concentration of sold suspended particles is proportional to the suspended particle quantity in a raw gas channel.

In FIG. 3, an arrangement is shown that serves for providing measurement gas that is free of volatile suspended particles and whose concentration of solid suspended particles is proportional to the suspended particle quantity in a raw gas channel. The arrangement combines principles of the two aspects of the invention cited above.

Raw gas is diverted from a raw gas channel 21 via a secondary raw gas channel 31 with the help of a pump 26. This diverted raw gas is heated and subsequently diluted on a first heating path 2. The dilution is effected here via a carrousel diluter 13 into a measurement gas channel into which dilution gas flows—in the FIG. 2 into the upper arm of the channel. A particle filter 22 may be connected upstream in order to ensure that the dilution gas is free of suspended particles. In the shown arrangement, a second heating path 2' is arranged downstream of the carrousel dilutor 13. The first and the second heating path 2, 2' may, for example, cooperate such that the desired temperature for the volatilization (for example alt least 180° C., preferably between 200° C. and 400° C.) is achieved only in or after the second heating path 2' and, thus, such that the first heating path serves consequently as a preheat stage in order, for example, to prevent the temperature of the raw gas falling below the dew point on entry into the secondary raw gas channel 31, by which means new volatile particles not yet present in the raw gas channel 21 would arise. A dilution gas preheat path 2'' may, for example, serve to preheat the dilution gas to roughly the same temperature as the raw gas. The temperature of the raw gas and of the dilution gas in front of the second heating path 2' is for example between 70° C. and 160° C. The first heating path as well as the dilution gas preheat path are optional in this embodiment.

As an alternative, in analogy to the embodiment described with reference to FIG. 1a, the raw gas may be heated by a first heating path 2 to a temperature, where the volatile particles evaporate, for example at least 180° C., preferably between 200° C. and 400° C. Also in this embodiment, there may optionally be a dilution gas preheat path and optionally a second heating path, for example for maintaining the measurement gas in a condition where the volatile particles do not precipitate.

A first measuring probe 11 for determining the volume flow is present in the raw gas channel 21. The controller 12 controls the supply of raw gas into the measurement channel 4, for example, such that the quantity of raw gas supplied to the measurement gas channel 4 per unit of time is proportional to the volume flow in the raw gas channel 21 and, as the case may be, also to the dilution gas volume flow in the measurement gas channel. The latter is determined by a second measuring probe 14. Further measuring probes 23, 24, 25 serve for determining the temperature and the pressure of the gases in the measurement and secondary raw gas channel. The values determined with these probes may, likewise, be included (not shown) in the control effected by the controller 12.

In the shown example, the first measuring probe 11 is attached in the raw gas channel 21 in the flow direction after the diverting of the secondary raw gas channel 31. The quantity of raw gas diverted into the secondary raw gas channel in many case is insignificant and may be neglected. One may, however, also carry out a suitable correction, for example the pump often delivers an exactly known volume per unit of time. Pressure and temperature measurements with measuring probes 24, 25 may also provide information on this. Alternatively to this, the first measurement probe 11 may be attached before the branching of the secondary raw gas channel.

In the drawing, a union 27 for introducing a calibration aerosol is further represented. Measurement systems present in the measurement gas channel 4 or connected downstream from this may be calibrated with this.

As in all other embodiments, any gas may be used as a dilution gas. Preferably it should essentially not have any suspended particles, i.e. the suspended particle concentration should be much lower that that of the raw gas. It is often useful to use filtered air as a dilution gas.

Figure 4:
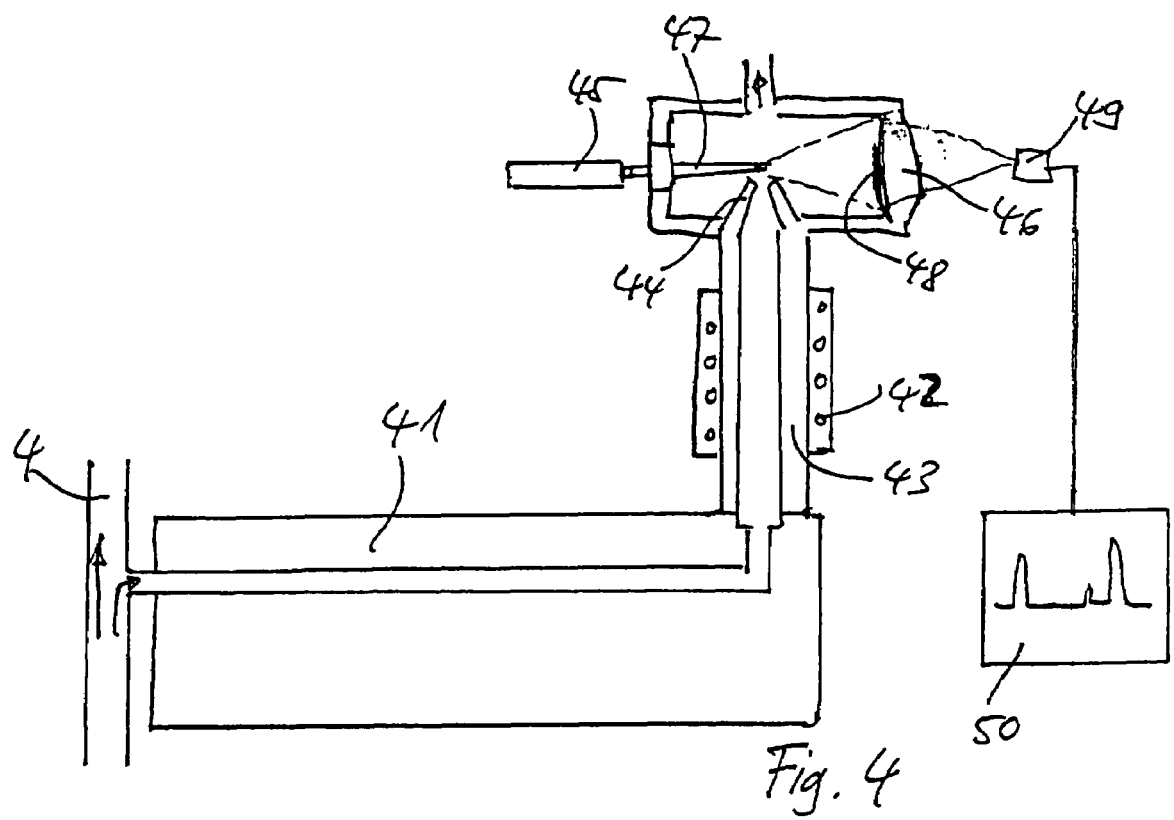
FIG. 4 is a schematic diagram of an embodiment of the third aspect of the invention.

Measurement units for characterizing the aerosol present in the measurement gas channel may connect to the measurement gas channel. These may be based on various physical principles and characterize physical and chemical properties of the suspended particles. For example, the light scattering on the particles, the diffused electrical charge on the particles, the photoelectrical gain, the movability etc. or also the particle mass may be analyzed. Several different measurement units may be connected in parallel, or under certain circumstances, may be arranged behind one another in series. A combination of various physical principles increases the conclusions which may be drawn from the measurements. A particularly preferred example of a measurement unit which may be arranged connecting to the measurement gas channel is a condensation nucleus counter according to a third aspect of the invention, which is to be discussed further below:

Hereinafter one embodiment of the third aspect of the invention is described. For this, FIG. 4 schematically shows a condensation nucleus counter for counting suspended particles. Condensation nucleus counters are known per se. For this reason, the details with regard to the apparatus and the manner of functioning of the condensation nucleus counter are described here only in a summarized form. It is to be understood that the third aspect of the invention may be combined with any known or new condensation nucleus counter.

A defined, generally small (for example approx. 1 l/min) quantity of measurement gas is diverted from the measurement gas channel 4 (the pumps, throttles, control means, etc. present for this are not shown). The measurement gas is deflected through a heated saturator 41 (the temperature for example being roughly 35° C.). In this saturator, the measurement gas comes into contact, for example, with a butanol-soaked sponge (of course instead of butanol other volatile substances are also conceivable). Subsequently, the measurement gas is led through a condenser 43 provided with cooling means 42 (the temperature for example being approx. 10° C.) where the butanol which is present supersaturated at the temperatures prevailing there condenses on the surface of the suspended particles. On account of the initially outlined limitations, this is only the case to a sufficient extent for suspended particles with a certain minimum radius. Following the condenser 43, the measurement gas goes through an exit nozzle 44 into a measurement chamber in which a light beam 47 produced by a light source 45—typically a laser diode—is focussed onto a measurement volume lying directly behind the exit opening of the exit nozzle 44. Light scattered on butanol droplets with a suspended particle as a condensation nucleus via focussing means 46 reaches a photo-detector 49. A screen 48 absorbs unscattered light. Light pulses produced by the photodetector reach an evaluation unit 50.

According to the invention, an evaluation according to scatter light intensities is effected in the evaluation unit 50 which may comprise means for amplification in an analog-electronic and/or digital/electronic manner, processing and/or conversion of signals as well as electronic data processing means. Indeed, it has been ascertained that such an evaluation provides indications on the reliability of the measurement. For illustration, two diagrams have been shown in the FIGS. 5a and 5b, which for various situations, represent the frequency (C) of the measurement pulses detected during a certain measurement duration as a function of the pulse intensity (I) (the diagrams are thus indeed histograms). The pulse intensity I is dependent on the particle size. Very small pulse intensities correspond to particles on whose surface not enough condensate could settle.

In both diagrams, $I_{th}$ represents the threshold intensity below which no or no longer reliable measurement results may be determined. 61 indicates the measured curve and 62 the frequency distribution in the no longer measurable region below the threshold intensity which in practice is thus no longer accessible. Pulses whose intensity lies below the threshold intensity are not detected on counting.

Figure 5A:
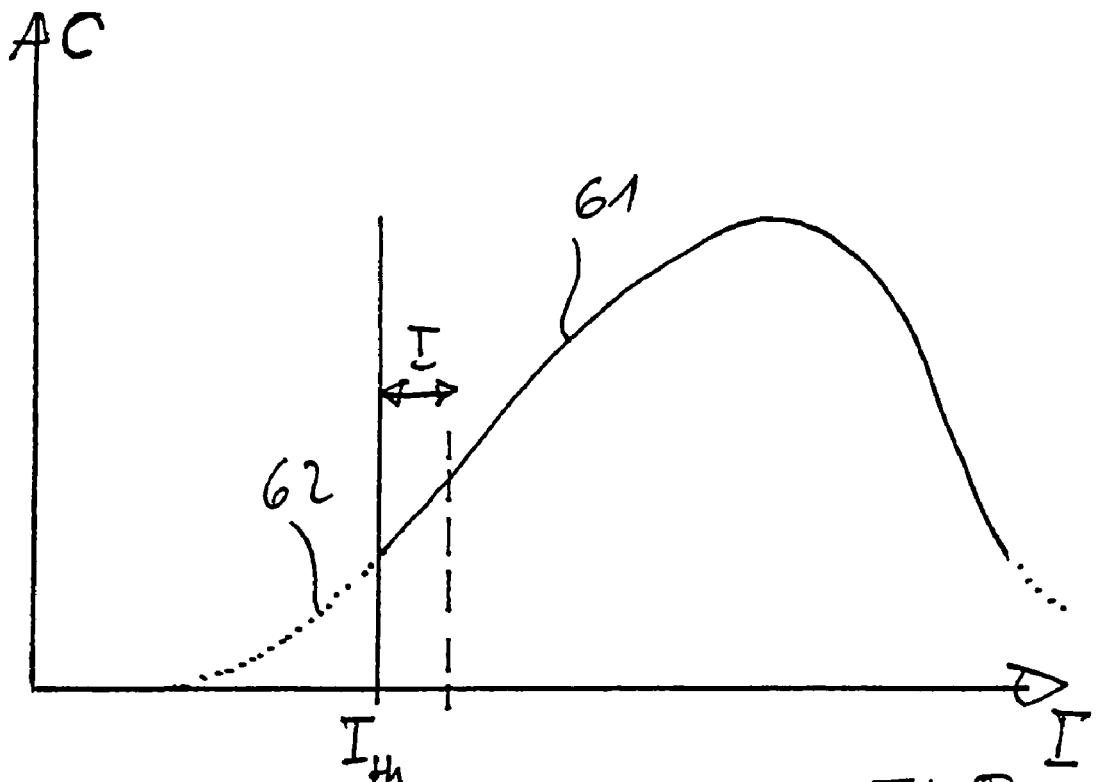
FIGS. 5a and 5b are fictive frequency distributions of scatter light pulses as a function of their intensity.
Figure 5B:
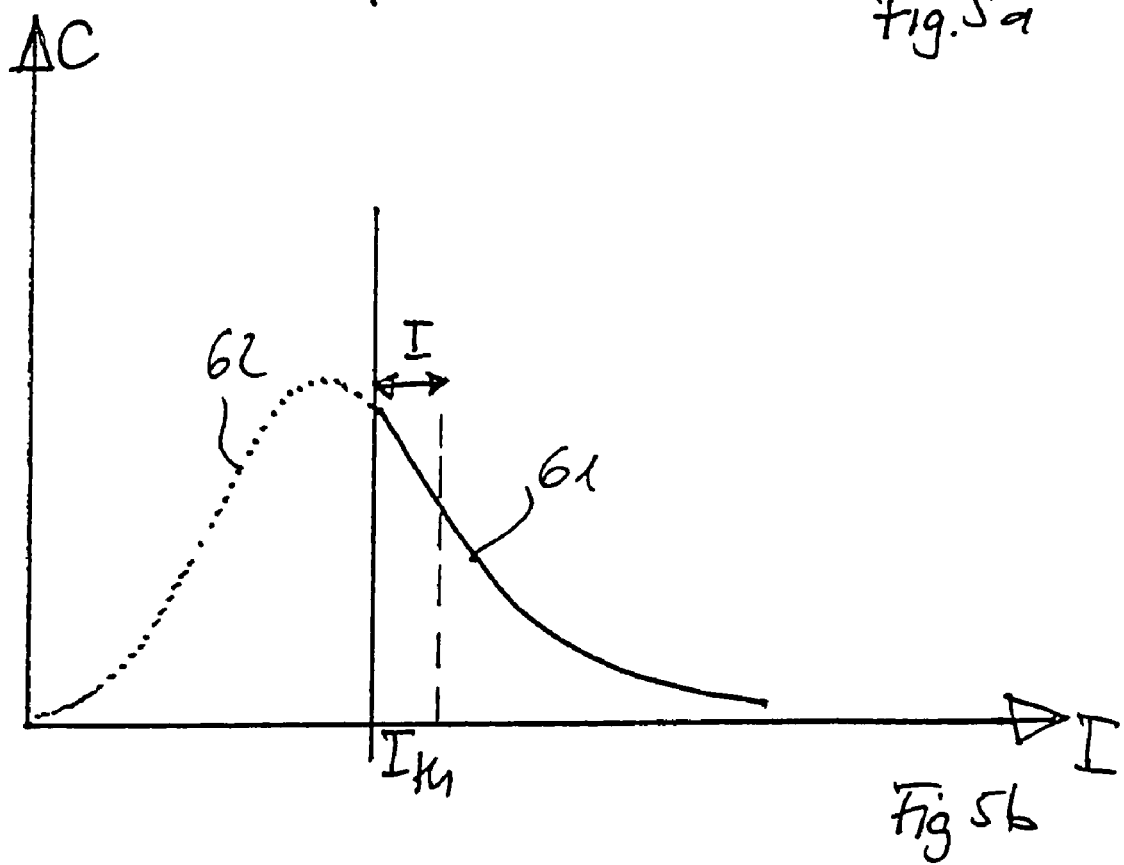

FIG. 5a represents the normal case. From the course of the measured intensity distribution 61, one may conclude with a very high reliability that the frequency of the non-measurable pulses (shown by the dotted line) is small. This is not so with a case as in FIG. 5b, where the measured frequency distribution 61 coming from large intensities does not significantly fall or even increases towards $I_{th}$. Here one must reckon with a large frequency in the non-measurable region. Accordingly, a measurement result that only counts the pulses lying in the measurable range (as in FIG. 5b) may no longer be used. It is to be rejected.

Solid suspended particles in waste gases of combustion motors are indeed always relatively "large", i.e. their size in each case is hardly below the detection threshold of modern condensation nucleus counters. The reason for this is the fact that a very high concentration of solid suspended particles prevails in the combustion space, by which means a coagulation into larger conglomerates compellingly takes place. The case is different, for example, with gas turbines. For this reason, a high concentration of "small" suspended particles often has one of the two following conclusions:

a. Volatile suspended particles are still present. If the third aspect of the invention discussed here has been combined with the first aspect of the invention, this generally means that an erroneous function is present, for example that the heating path is not sufficiently heated.
  b. "Unusual" solid suspended particles are present which need to be further examined with other measurement methods. Such may for example be effected by additives in the fuel, for example cer-additives which are sometimes used.

The decision as to whether a measurement result may be used or must be rejected may be made by way of the frequency distribution (as a function of the pulse intensity) in various manners. For example, the frequency of pulses that are measured in a certain intensity interval I lying below the threshold value is determined and set in relation to the measured total intensity. The measurement is rejected if the share of pulses measured in the intensity interval I exceeds a certain presettable percentage. Alternatively to this, one may also determine the gradient of the C(I) curve in the vicinity of $I_{th}$ and, for example, reject the measurement if it is negative, or the maximum of the C(I) curve may be compared to the value at $I_{th}$, etc.

The device according to the third aspect of the invention accordingly comprises means for the electronic analysis of the frequency distribution so that on account of the frequency distribution, one may draw conclusions on the frequency of the particles below the one certain threshold size.

Concluding, according to a first aspect of the invention, volatile suspended particles are eliminated in that in a first step the aerosol is heated to a temperature at which the volatile suspended particles evaporate and in a second step the aerosol may be diluted with a dilution gas. The sequence of the first and of the second step may be exchanged. According to a second aspect of the invention, a dilution of the raw gas takes place such that raw gas is supplied to a measurement gas channel through which measurement gas flows, wherein the quantity of raw gas transferred per unit of time is dependent on the volume flow in the raw gas channel. According to a third aspect of the invention, not only is the number of measured scatter light pulses, but also their intensity, evaluated in a condensation nucleus counter in order to be able to draw conclusions on the reliability of the measurement.

Units for realizing the first, second and third aspect may be combined with one another which bring advantageous results. Such units, however, either alternatively or in a supplementary manner, may also be combined with further methods and devices for characterizing, separating and eliminating aerosols—those according to the state of the art or ones to be newly developed. A combination of the first and the third aspect of the invention is particularly advantageous with regard to reliable measurements of the particle number of only the solid suspended particles or a combination of the first and of the second aspect of the invention or also of the second and third aspect with regard to the reduction of the scope and energy consumption of an installation for measuring harmful suspended particles.

What is claimed is:

1. A device for characterising, separating and/or eliminating suspended particles in a carrier gas of an aerosol wherein the aerosol contains solid suspended particles and volatile suspended particles, comprising:
   a gas supply and a gas discharge,
   further comprising heating means for heating the aerosol to a temperature at which volatile suspended particles evaporate, but the solid suspended particles are unaffected,
   a dilution unit for diluting the aerosol with a dilution gas, wherein, referring to a flow direction of the aerosol, the dilution unit is arranged upstream of the heating means, and
   further comprising a measuring unit arranged downstream of the dilution unit and the heating unit, the measuring unit being capable of measuring either the characteristics of or the quantity of the unaffected solid suspended particles, or both, remaining in the aerosol downstream of the dilution unit and the heating unit.

2. A device for characterising, separating and/or eliminating suspended particles in a carrier gas of an aerosol wherein the aerosol contains solid suspended particles and volatile suspended particles, comprising:
   a gas supply and a gas discharge,
   further comprising heating means for heating the aerosol to a temperature at which volatile suspended particles evaporate, but the solid suspended particles are unaffected,
   a dilution unit for diluting the aerosol with a dilution gas,
   further comprising a measuring unit arranged downstream of the dilution unit and the heating unit, the measuring unit being capable of measuring either the characteristics of or the quantity of the unaffected solid suspended particles, or both, remaining in the aerosol downstream of the dilution unit and the heating unit, and
   further comprising a saturator downstream of the heating means and of the dilution unit, in which the aerosol may be provided with a volatile substance and a condenser in which conditions prevail by way of which the volatile substance may be brought to supersaturation, a measurement volume in which the suspended particles from the condenser may be guided through a light beam, and detection means for detecting scatter light pulses that are caused by the scattering of light of the light beam on suspended particles, further comprising evaluation means that are designed for evaluating scatter light pulse intensities.

3. A method for detecting and characterising solid suspended particles in a carrier gas of an aerosol wherein the aerosol contains volatile suspended particles, comprising the steps of:
   diluting the aerosol with a dilution gas thus forming a diluted mixture, and
   heating the diluted mixture to a temperature at which volatile suspended particles evaporate, but the solid suspended particles are unaffected, thus forming a modified diluted mixture,
   analyzing at least a representative portion of the modified diluted mixture to detect the presence of any solid suspended particles therein, and if present measuring either the characteristics of or the quantity, or both, of the unaffected solid suspended particles.

* * * * *